US008827941B2

(12) United States Patent
Davis et al.

(10) Patent No.: US 8,827,941 B2
(45) Date of Patent: Sep. 9, 2014

(54) BELOW-KNEE LEG PROTECTOR

(76) Inventors: William Davis, Utica, MN (US);
Michael Vitse, Rochester, MN (US)

( * ) Notice: Subject to any disclaimer, the term of this patent is extended or adjusted under 35 U.S.C. 154(b) by 323 days.

(21) Appl. No.: 13/385,133

(22) Filed: Feb. 3, 2012

(65) Prior Publication Data
US 2013/0204396 A1 Aug. 8, 2013

(51) Int. Cl.
*A61F 13/00* (2006.01)
(52) U.S. Cl.
USPC ............................................. 602/62; 602/60
(58) Field of Classification Search
CPC ........... A61F 2/64; A61F 2/78; A61F 2/7812; A61F 2/80; A61F 13/00; A61F 13/06; A61F 13/061; A61F 13/08; A61F 13/14; A61F 5/00; A61F 5/0123; A61F 5/0125
USPC ....................... 602/60–6, 264, 60–64, 23, 26; 623/31–37; D2/980
See application file for complete search history.

(56) References Cited

U.S. PATENT DOCUMENTS

| | | | | |
|---|---|---|---|---|
| 2,202,598 A * | 5/1940 | Peterson | ......................... | 623/32 |
| 3,138,156 A * | 6/1964 | Crowell et al. | ................. | 602/61 |
| 3,186,006 A * | 6/1965 | Miller | .............................. | 623/36 |
| 3,451,232 A * | 6/1969 | Belzidsky | ........................ | 66/171 |
| 3,600,717 A * | 8/1971 | McKeehan | ....................... | 602/61 |
| 4,644,946 A * | 2/1987 | Cremona-Bonato | ........... | 602/61 |
| 4,840,635 A * | 6/1989 | Smith et al. | ...................... | 623/36 |
| 4,842,608 A * | 6/1989 | Marx et al. | ...................... | 623/33 |
| 5,314,496 A * | 5/1994 | Harris et al. | .................... | 623/31 |
| 5,376,130 A * | 12/1994 | Courtney | ........................ | 623/33 |
| 5,507,722 A * | 4/1996 | Richardson | ..................... | 602/62 |
| 5,728,165 A * | 3/1998 | Brown, Sr. | ...................... | 623/33 |
| 7,575,561 B2 * | 8/2009 | Smith et al. | ..................... | 602/60 |
| 7,641,625 B2 * | 1/2010 | Nobbe | ............................ | 602/63 |
| 2005/0101693 A1 * | 5/2005 | Arbogast et al. | .............. | 523/122 |
| 2011/0201985 A1 * | 8/2011 | Entler | ............................. | 602/62 |
| 2012/0191028 A1 * | 7/2012 | Entler | ............................. | 602/63 |

* cited by examiner

*Primary Examiner* — Kim M Lewis
(74) *Attorney, Agent, or Firm* — D L Tschida

(57) ABSTRACT

A multi-piece therapeutic cover that assembles to warm, cushion and stabilize the thigh of a below-knee amputee. A thigh piece contains a resiliently rigid channel piece and several laterally extending, wings including sizing tabs that overlap and cooperate with associated straps. A stump contact piece, end cap piece and knee cover piece contain foam pads to cushion the stump end and knee. Strips of hook and loop fastener material arrayed about the surfaces of the protector pieces judiciously overlap to contain the protector pieces to each other and the limb. Buckled straps further support the protector assembly to the limb.

19 Claims, 4 Drawing Sheets

BELOW-KNEE LEG PROTECTOR

BACKGROUND OF THE INVENTION

The present invention relates to limb protection devices for amputees and, in particular, to a multi-piece, padded, fabric and fleece lined assembly for below-knee amputees, wherein a leg or thigh piece, a stump contact piece, a distal end cap cover piece and a knee or patella cover piece contain resilient contoured inserts and/or foam cushion pieces that support/ brace and cushion the thigh, knee and stump end and wherein hook and loop fasteners and stabilizing straps organize and secure the pieces to each other and to the amputee's limb.

A variety of appliances have been developed for amputees for use during post-operative recovery, therapy and long term maintenance. The devices are typically constructed for particular use with the arms and legs. Some devices serve as dressings during recovery. Some devices mount to the limb to stabilize the stump end and support or cushion a prosthesis mounted to the limb. Some devices include active linkages that cooperate with and stabilize limb movement. U.S. Pat. Nos. 5,302,169; 5,529,575; 5,571,206 and 5,651,792 disclose devices having active, hinged linkage pieces adapted for use by below-knee amputees.

Some appliances are used daily after removal of a prosthesis to cover, warm and/or protect the limb and stump, such as during periods of relative inactivity (e.g. when at home or asleep). It is to the latter category that the subject invention belongs. The assembly of the present invention is intended to mount to and warm an amputated limb to promote vasodilatation, maintain blood circulation and prevent ulceration or other physical degradation of the stump. That is, by keeping the limb and stump end warm, the blood vessels don't constrict and healthy blood flow is maintained. The device also physically cushions and warms the limb with minimal skin trauma (e.g. ulcerations, cracking and/or abrasions).

The present below-knee limb protector assembly was developed to provide a multi-piece light weight assembly that warms, cushions and stabilizes the extremity. The assembly includes a thigh piece having a longitudinal support portion containing a rigid channel member constructed from a resilient and malleable material and several laterally extending cloth covered wings having fasteners that overlap to encase the limb and cooperate with associated strap fasteners. A stump contact piece, end cap piece and knee or patella cover piece contain foam pads to cushion the stump end and knee. Strips of hook and loop fastener material are arrayed about the protector pieces and judiciously overlap to contain the protector pieces to each other and the limb. Buckled straps further support the protector to the limb.

SUMMARY OF THE INVENTION

It is accordingly a primary object of the invention to provide a thermally insulated protection assembly for below-knee amputees to stabilize, cushion and warm the limb to stimulate blood circulation.

It is a further object of the invention to provide a below-knee protective assembly comprising several sewn fabric and fleece pieces having a number of hook and loop fasteners fitted to overlapping surfaces of the assembly pieces and associated straps to collectively wrap and fasten to configure and encase the protective device about the thigh.

It is a further object of the invention to provide a protective device having a thigh piece that contains a longitudinal, foam covered, contoured, resilient channel member shaped to contain and support the thigh.

It is a further object of the invention to provide a thigh support piece wherein overlapping fleece lined fabric wings contain multiple separated lines of stitching that segregate the wings to accommodate tailor fitting the assembly; presently the stitching is positioned to accommodate differing circumferential limb sizes and wherein the stitching transversely bisects each wing piece and is displaced sufficiently (e.g. 1 to 4-inches) to segment each wing and permit shortening the wing pieces adjacent the stitching without fraying to tailor the length of the wing pieces to fit the circumference of the amputee's limb.

It is a further object of the invention to provide stump contact cushions, spacers and adjoining end cap pieces that provide cloth/fleece covered foam cushions that directly contact the stump end and/or fill a space between the contact piece and an end cap piece to conform to and cushion the stump end and fasten to a limb encasing thigh piece.

It is a further object of the invention to provide a knee or patella cover support piece that contains a foam cushion and mounts to a limb encasing thigh piece.

The foregoing objects, advantages and distinctions of the invention are obtained in a presently preferred fabric covered limb protector assembly of the invention that is lined with fleece. One or more pieces can also contain a thermal insulation. Several overlapping tabs of hook and loop fastener material are arrayed about the surfaces of several wing pieces at a thigh cover piece and detachable knee and end cap fabric cover pieces and mate with other associated fastener pieces and straps. The fasteners at the wings of the thigh piece and detachable knee and end cap pieces align to define and selectively control the fitting of the protective assembly to the amputee's thigh and stump.

The thigh piece contains a longitudinal foam covered, rigid channel member constructed from a resilient and malleable material having a contoured channel that supports the posterior surface of the thigh and knee. Laterally extending wing portions extend such that the thigh piece exhibits a general "H" shape. The wing pieces include displaced lines of transverse stitching organized and arranged to permit cutting and shortening the wing pieces to fit different thigh circumferences. The length of at least one wing piece can thereby be tailored to assure a proper fit about the circumference of an amputee's thigh upon wrapping and overlapping the wing pieces onto each other.

Hook and loop fasteners are secured to external fabric and internal fleece surfaces of the assemblies' pieces and are aligned to overlap and secure the protective assembly to the amputee's thigh. Other accessory, extension pieces having tabs of hook and loop fastener material can be mounted to the thigh piece wings to extend the wings to fit amputees with large diameter thighs.

A stump cover or end cap piece contains a foam cushion and provides a fleece liner and mates to the stump end. Associated fabric/fleece covered foam spacers can be added to fill the longitudinal space of the thigh piece.

An end cap piece contains a foam cushion and wing pieces that support tabs of hook and loop fastener material and mount to the thigh piece to contain the stump cover and filler pieces to the thigh cover piece.

A fabric and fleece covered knee or patella cover piece contains a foam cushion and supporting sewn strips and straps of hook and loop fastener material that overlap and mount to the thigh piece to cover the knee.

Still other objects, advantages, distinctions and constructions of the invention will become more apparent from the following description with respect to the appended drawings. Similar components and assemblies are referred to in the various drawings with similar alphanumeric reference characters. The components can be combined in various combinations and with other limb protection assemblies. The description should therefore not be literally construed in limitation of the invention. Rather, the invention should be interpreted within the broad scope of the further appended claims.

Figure 1:
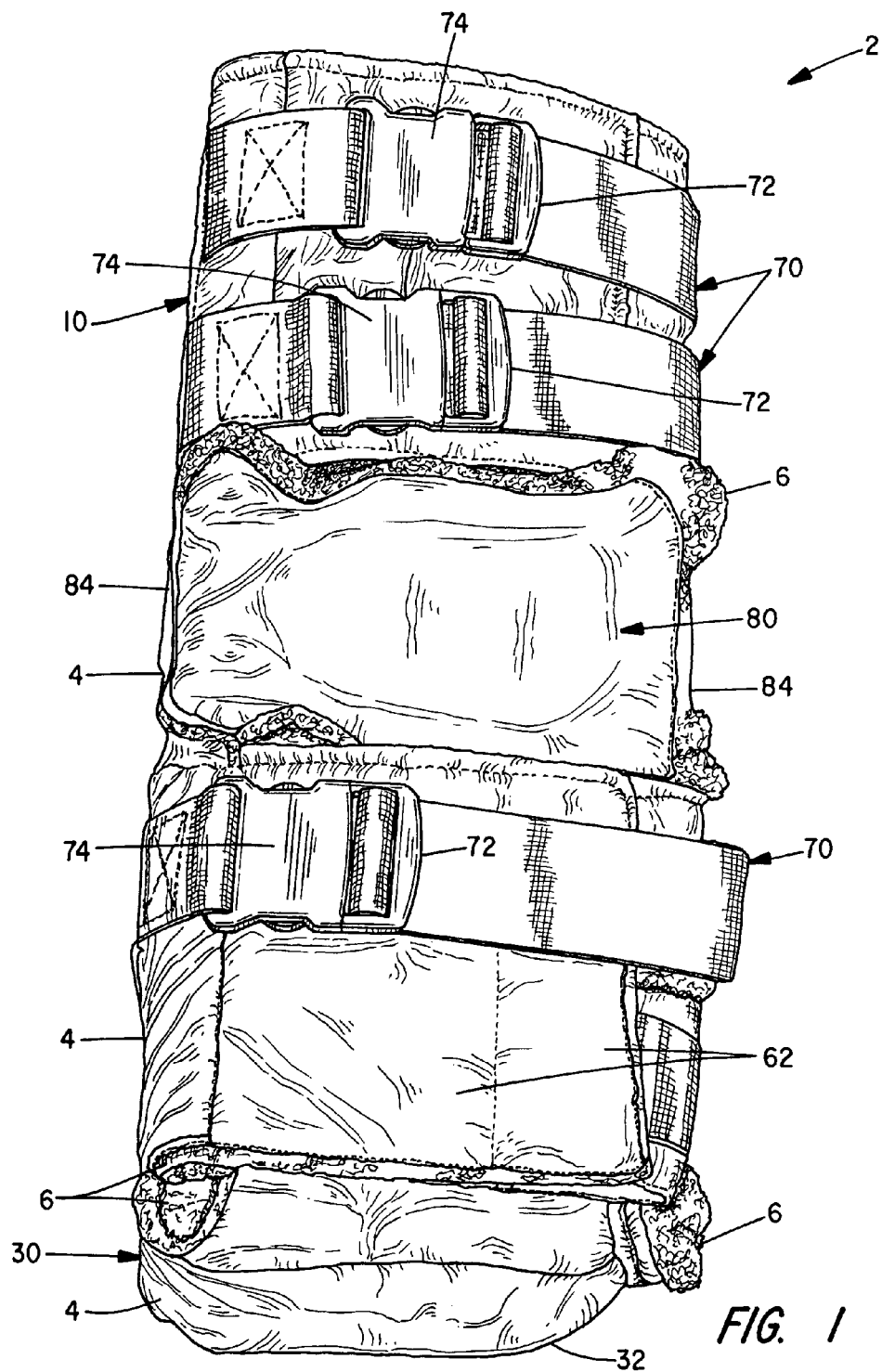
FIG. 1 is a perspective drawing of the leg protector assembly removed from an amputee's leg and wrapped and buckled to a closed condition with the knee and end cap pieces mounted to the leg or thigh cover piece.

Similar structure throughout the drawings is referred to with the same alphanumeric reference numerals and/or characters.

DESCRIPTION OF THE PREFERRED EMBODIMENT

Referring to FIGS. 1-4 several perspective views are shown in various stages of assembly to the present invention of a therapeutic leg protector assembly 2 for partial leg (e.g. below-knee) amputees. The leg protector assembly 2 is constructed of several sections or pieces that assemble to form the protector 2 shown removed from a wearer's leg in a fully assembled condition in FIG. 1. The several pieces of the protector 2 are constructed from an air permeable fabric cover material 4. The cover material 4 is presently sewn from a durable velour cloth. Other materials such as a heavyweight cotton fabric, CORDURA® or other fabrics or laminated/layered fabric and insulation combinations might also be used.

The interior surface of the cover material 4 is lined with a fleece material 6. A thermal insulation material 8 shown in partial cutaway at FIG. 2, if desired, can also be mounted between the cover material 4 and the interior fleece lining 6. A suitable thermal insulation material 8 can for example comprise THINSULATE® or any of a variety of other cushioning and insulating materials. The fleece 6 and any provided insulation material 8 collectively provide a thermal barrier to maintain the temperature of a covered limb 9 to promote dilation of the blood vessels and blood flow through the covered extremity.

The leg protector 2 when fitted to an amputated limb, such as the leg or thigh, is assembled from a number of separate pieces that are positioned to the limb and sequentially overlapped and fastened or attached to each other. When fully assembled the protector 2 covers, warms and protects the amputee's limb.

Figure 2:
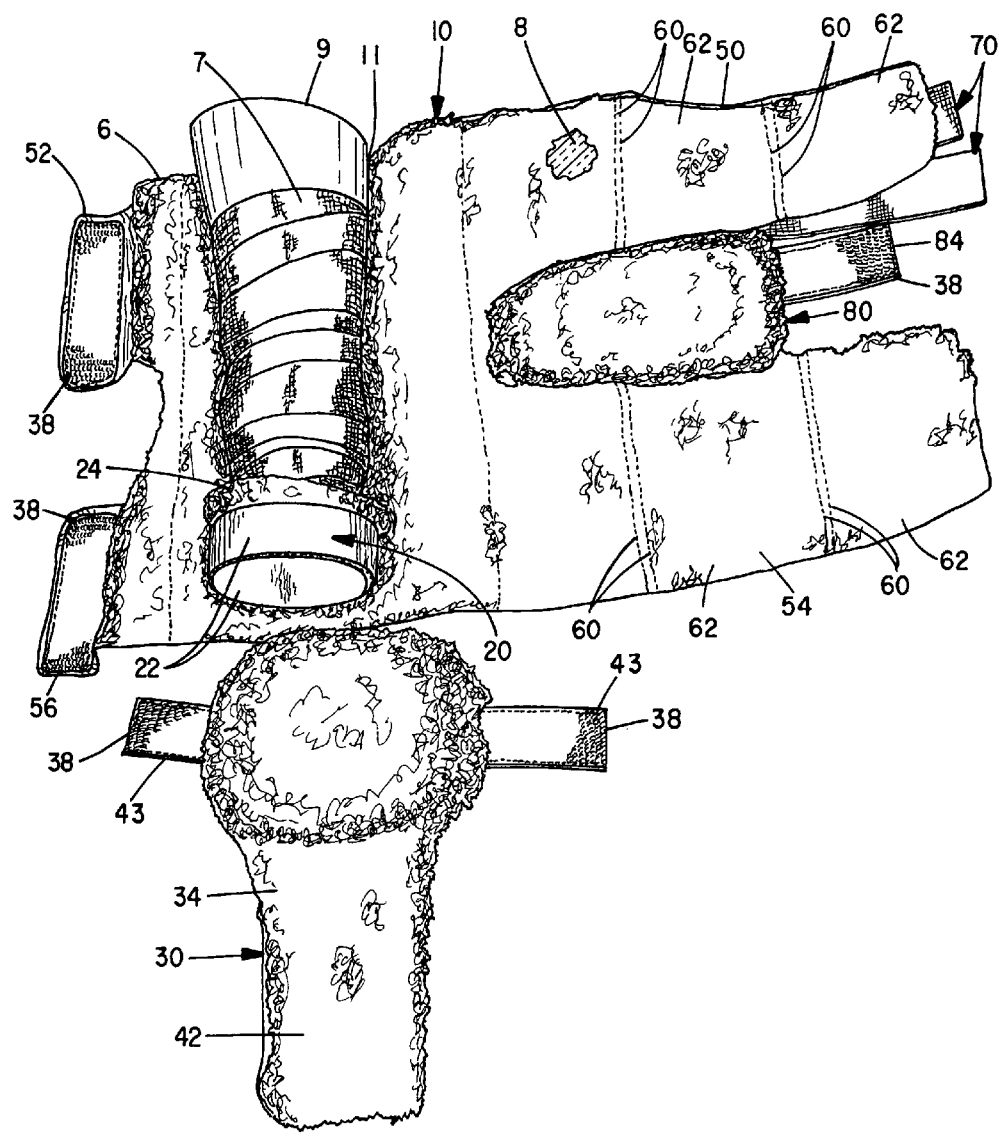
FIG. 2 is a perspective drawing of the leg protector assembly folded open and showing the relative positioning of a portion of an amputee's leg to the leg or thigh cover, the knee cover, stump cover, and end cap pieces and an accessory foam filler pad that mounts between the stump cover and end cap pieces and wherein a cutaway view is shown to an internal foam cushioning and/or a possible thermal insulation/cushioning material.

With attention to FIG. 2 and during fitting, an elongated, "H-shaped" leg or thigh piece 10 is typically laid out and the wearer's limb 9 is aligned to lie in a longitudinal center portion that defines a channel or trough space 11. The trough space 11 exhibits a contoured curvature (e.g. arcuate) when viewed end on. The curvature is defined by a resiliently rigid, generally "U-shaped" channel or trough member 12 contained in the longitudinal center portion of the thigh piece 10, see FIG. 3. Prior to mounting the protector assembly 2, the limb 9 can be wrapped with a gauze material or other suitable cover or sock 7 can be mounted to the limb.

The channel member 12 extends substantially the length of the thigh piece 10. The channel member 12 is presently constructed of a resilient plastic material. The material is generally rigid but can flex laterally and torsionally without breaking. A variety of different plastics, KEVLAR®, polymers, compositions or metal materials can be used to form the channel member 12. The contour of the channel shape might also be adjusted depending upon the limb and for example might be molded or formed into a preferred shape prior to or after mounting in the thigh piece 10. Depending upon the material, heat or other external energy sources can be used to tailor contour the channel space 11.

One or both of the posterior and anterior surfaces of the channel member 12 can be covered with a layer of foam 14. The channel member 12 mounts in a longitudinal pocket defined by lines of stitching formed between the cover and fleece liner materials 4 and 6. The limb 9 (e.g. leg or thigh) of an amputee when fitted to the thigh piece 10 nests in the curvature of the channel space 11 and the internal fleece lining 6 and underlying foam layer 14 conform about the limb 9. The thigh and knee are simultaneously supported in coaxial alignment with the channel space 11 and the knee is generally immobilized.

Once the thigh and knee are fitted into the thigh piece 10 a space can exist at the end of the amputee's stump. A stump contact cover piece 20 is then positioned in the space to contact the distal or stump end of the limb. The stump cover piece 20 provides a fabric cover 22 and fleece liner 24 that are sewn together to contain a generally cylindrical foam pad 26. The fleece end 24 is mounted to contact the stump end. Depending upon the length of the limb relative to the thigh piece 10, one or more cloth covered foam filler pieces 26 can be mounted distal to the stump contact cover piece 20, see FIG. 4.

An end cap piece 30 having a fabric cover 32 and fleece lining 34 and containing a foam pad 36 is next fastened to the thigh cover piece 10. Tabs of hook and loop fastener material 38 and 40 that are adhered or affixed such as by sewing to the fleece lining 34 and fabric cover material 4 of the thigh piece 10 are overlapped and fastened together to hinge the end cap piece 30 to the thigh piece 10. The end cap piece 30 can thereby pivot relative to the distal end of the thigh piece 10 to align the foam pad 36 of the end cap 30 with the stump cover piece 20 and any filler pieces 26.

A tongue portion 42 extends from the end cap piece 30 and independently folds to mount over the anterior surface of the contained limb 9 and stump cover piece 20. Wings or straps 43 of hook fastener material 38 laterally extend from the end cap piece 30 and separately attach to longitudinal tabs of loop fastener material 40 attached to external sides of the thigh piece 10. Upon folding the tongue 42 over the stump end and stump cover 20 and securing the fastener straps 43 to the thigh piece 10, the stump contact piece 20 and filler pieces 26 are held in place.

The remainder of the limb protector pieces are next arranged and secured to each other to fully secure the protector assembly 2 to the amputee's limb. The thigh piece 10 is secured to the limb and end cap piece 30 with upper and lower wing or arm portions 50 and 52 and 54 and 56 that extend from longitudinal sides of the thigh piece 10. The relatively short side arm portions 52 and 56 extend approximately 1 to 2-inches and contain tabs of appropriate hook/loop fastener material 38 or 40 sewn to the fleece lining 6.

The relatively longer upper arm portions 50 and 54 are constructed to lengths on the order of 8 to 14-inches to accommodate thighs of differing circumference. The arm portions 50 and 54 include displaced lines of sewn stitching 60 that segment and define a series of tabs 62 at each arm portion 50 and 54. A tab 62 can be severed from the thigh piece 12 by cutting between the lines of stitching 60 or in other fashions without producing fraying at the severed edges. The paired lines of stitching 60 separate the wing arms 50 and 54 into several tabs 62 and each tab sized in a range of approximately 2 to 4 inches in length. Depending upon the amputee, one or more tabs 62 can be severed to tailor fit the length of the wings 50 and 54 to the circumference of the bound limb. The extraneous tabs 62 are severed at or between the stitching lines 60 without fraying or separation of the fabric and fleece layers 4 and 6. It is to be appreciated single lines of stitching 60 might also be used to accommodate tailor fitting.

Upon wrapping the wing arms 52 and 56 over the limb and overlapping the arms 52 and 56 with the arms 50 and 54, tabs of appropriate hook/loop fastener material 38 or 40 sewn to the fabric cover material 4 and fleece lining 6 at the arms 52 and 56 mate with the fastener tabs at the arms 50 and 54 to secure the thigh piece 8 to the limb 9. The overlapped arms 52 and 56 also bind the tongue portion 42 of the end cap piece 30 to the limb.

Figure 3:
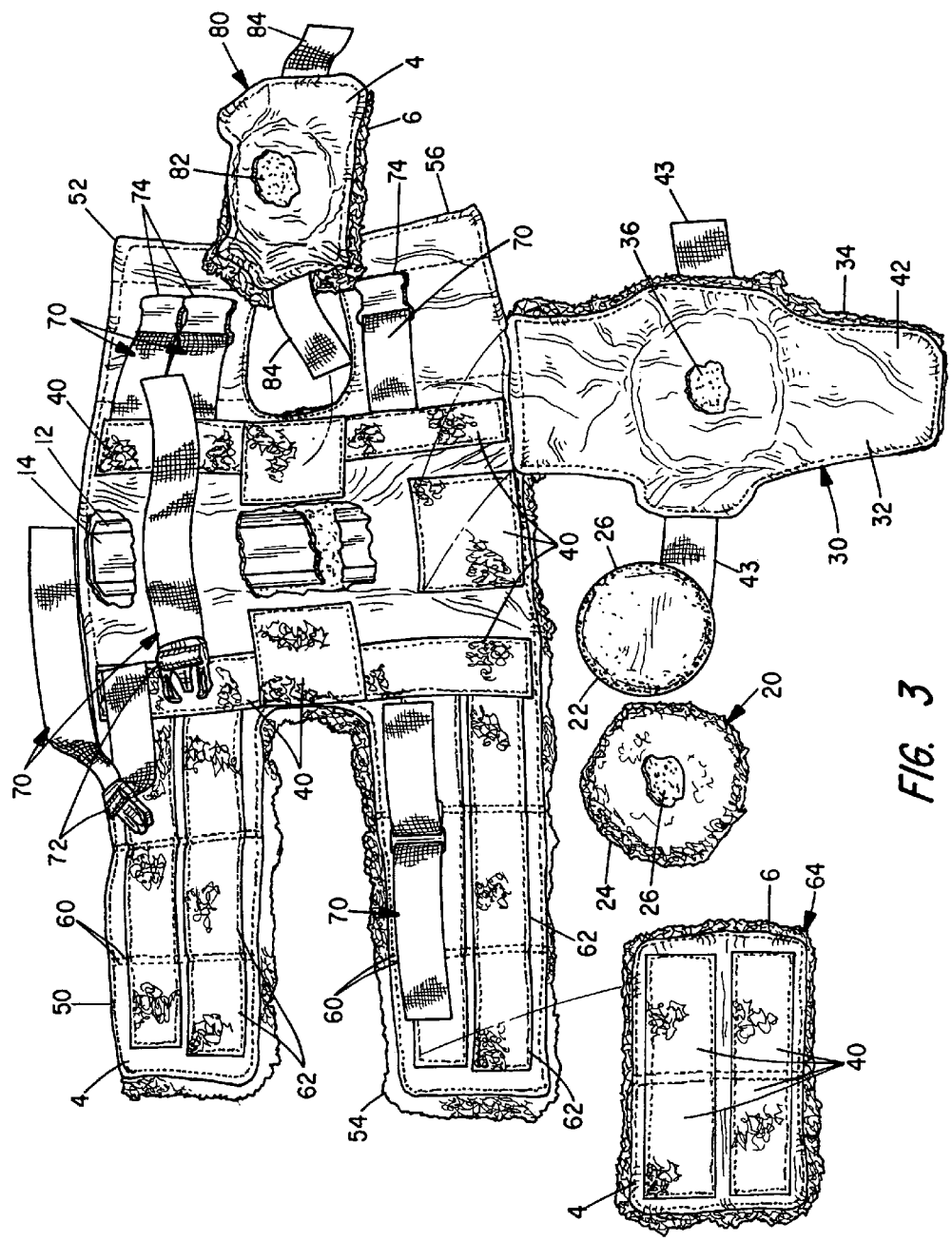
FIG. 3 is a rear perspective drawing of the leg protector assembly folded open with the knee and end cap cover pieces detached, along with a detached thigh wing extension piece and wherein cutaway views depict an elongated rigid thigh channel support member and foam cushioning liners mounted in the thigh cover piece and several foam pads mounted in the knee cover, stump cover and end cap pieces.
Figure 4:
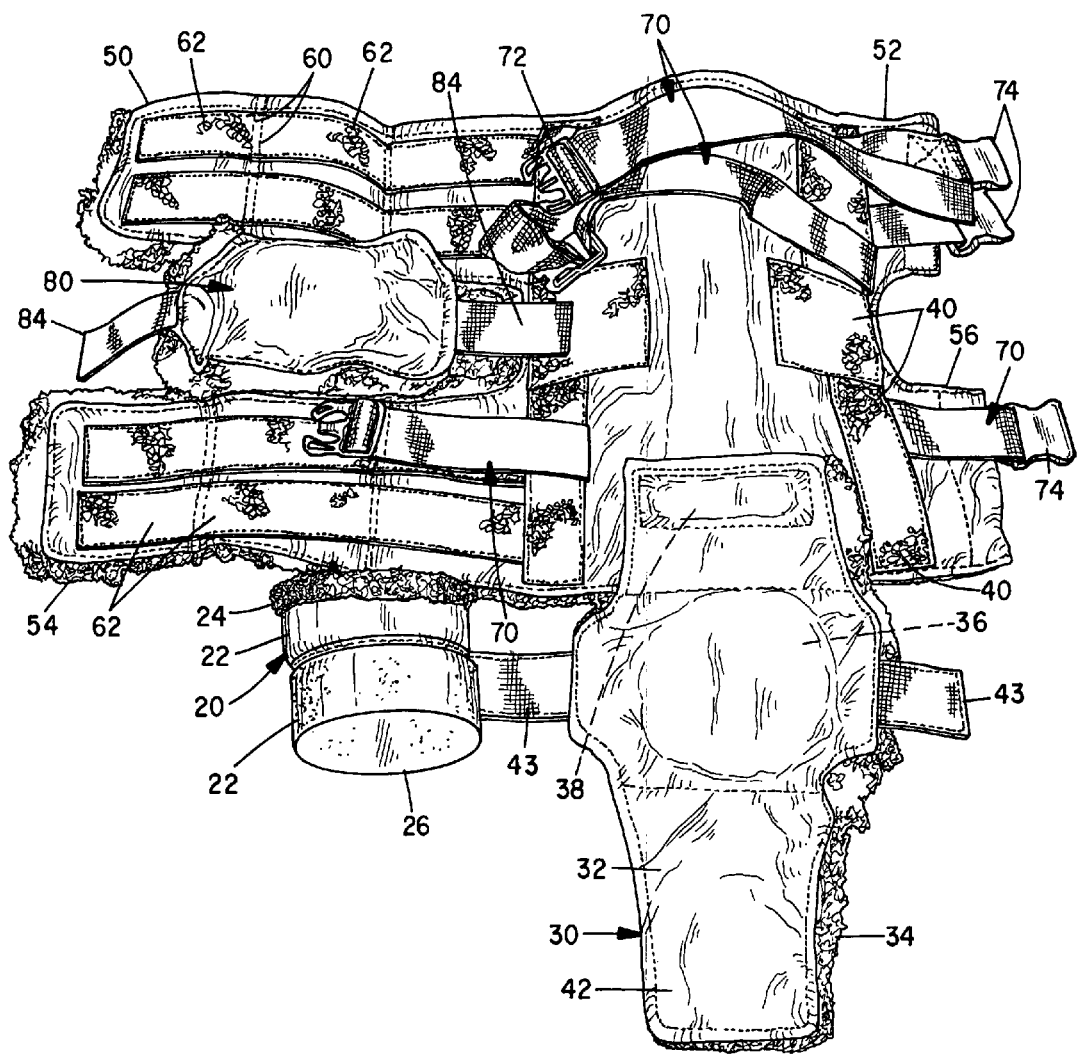
FIG. 4 is a rear perspective drawing of the leg protector assembly folded open with the knee and end cap cover pieces attached to the thigh cover piece and wherein stump cover end cap and spacer pieces are shown removed from the assembly.

One or more fabric 4 and fleece 6 covered wing extension pieces 64 (one of which is shown at FIG. 3) can be fastened to the arms 50-56 to appropriately extend the length of the overlapping combined arm pieces 50, 52 and 54, 56 to fit amputees having thighs of large circumferences.

The protector assembly 2 is further secured to an amputee's limb by additionally wrapping buckled straps 70 sewn to the cover material 4 at the wing arms 50-56 to independently overlap the fastened wing arms 50-56. Mating buckles 72 and 74 sewn to the ends of the straps 70 are then fastened to securely attach the thigh piece 10 to the amputee's limb, see FIG. 1. A variety of different types of mating buckles and fasteners can be used to secure the ends of the straps 70.

A knee or patella cover piece 80 is next affixed to the thigh piece 10. The knee cover piece 80 comprises an envelope of fabric 4 and fleece 6 material that contain a foam cushion piece 82. Straps 84 extend from the fabric cover material 4 and support tabs of hook/loop fastener material 38 and/or 40. The knee cover piece 80 is mounted over the wrapped thigh cover 10 to cover the amputee's knee and the straps 84 are secured to the longitudinal tabs of hook/loop fastener material 38 and/or 40 that extend along the sides of the thigh piece 10.

While the invention has been described with respect to a number of preferred constructions and considered improvements or alternatives thereto, still other constructions may be suggested to those skilled in the art. It is also to be appreciated that selected ones of the foregoing features can also be used singularly or be arranged in different combinations to provide a variety of improved therapeutic limb wear. The foregoing description should therefore be construed to include all those embodiments within the spirit and scope of the following claims.

What is claimed is:

1. A therapeutic cover apparatus for an amputated leg comprising:
    a) a fabric thigh piece having a longitudinal center portion containing a rigid channel member exhibiting an arcuate longitudinal channel adapted to support an amputee's leg, wherein a plurality of fabric wings having mating fasteners laterally extend from said center portion to wrap about and circumscribe an amputee's leg, overlap and fasten together to encase and secure the thigh piece to an amputee's leg;
    b) a fabric stump contact piece containing a foam pad and adapted to mount interiorly of the wrapped thigh piece to cushion a stump end of an amputee's leg; and
    c) a fabric end cap piece containing a foam pad and adapted to directly attach to said thigh piece to cover and secure said stump contact piece within the wrapped thigh piece.

2. The therapeutic cover apparatus as set forth in claim 1 including a fabric patella cover piece containing a foam cushion and adapted to cover and cushion an amputee's patella.

3. The therapeutic cover apparatus as set forth in claim 1 wherein said thigh, stump contact, and end cap pieces comprise fleece lined fabric panels.

4. The therapeutic cover apparatus as set forth in claim 3 wherein said thigh and end cap pieces contain a plurality of tabs of hook and loop fastener material affixed to the fabric and fleece surfaces of said thigh and end cap pieces and wherein the tabs are arranged to overlap and fasten together.

5. The therapeutic cover apparatus as set forth in claim 3 including a thermal insulation material mounted between the fabric and fleece layers of said thigh and end cap pieces.

6. The therapeutic cover apparatus as set forth in claim 3 wherein said channel member is formed from a malleable material adapted to permit the tailoring of the contour of said channel.

7. The therapeutic cover apparatus as set forth in claim 1 wherein a plurality of straps containing mating fasteners are displaced along a length of said thigh piece and mount to circumscribe and bind said thigh piece to an amputee's leg.

8. The therapeutic cover apparatus as set forth in claim 1 wherein the plurality of the wings of said thigh piece include a plurality of displaced parallel lines of stitching arranged to segregate each wing into a plurality of tabs and wherein a length of each wing can be tailored without fraying to the circumference of an amputee's limb upon severing one or more tabs from one or more wings at said lines of stitching.

9. The therapeutic cover apparatus as set forth in claim 1 including a foam filler piece adapted to mount interiorly of said thigh piece between said stump contact and end cap pieces.

10. The therapeutic cover apparatus as set forth in claim 1 including an extension piece supporting a plurality of fasteners adapted to mount to the wings of said thigh piece to extend a length of a conjoined wing to wrap about an enlarged circumference of an amputee's leg.

11. A therapeutic cover apparatus for an amputated leg comprising:
    a) a fabric thigh piece having a longitudinal center portion containing a rigid channel member exhibiting an arcuate longitudinal channel adapted to support an amputee's leg, wherein a plurality of fabric wings having mating fasteners laterally extend from said center portion to wrap about and circumscribe an amputee's leg, overlap and fasten together to encase and secure the thigh piece to an amputee's leg, wherein said fabric thigh piece and plurality of wings are lined with a fleece material, and wherein said channel member is secured in a pocket between an external fabric layer and an internal fleece layer of said center portion;

b) a fleece lined fabric stump contact piece containing a foam pad and adapted to mount interiorly of said thigh piece to cushion a stump end of an amputee's leg;

c) a fleece lined fabric end cap piece containing a foam pad and adapted to directly attach to said thigh piece to cover and secure said stump contact piece within the wrapped thigh piece; and d) a fleece lined fabric patella piece containing a foam cushion and adapted to directly fasten to said thigh piece to cover and cushion an amputee's patella.

12. The therapeutic cover apparatus as set forth in claim 11 wherein said thigh, end cap and patella pieces contain a plurality of tabs of hook and loop fastener material mounted to surfaces of said fabric and fleece layers to overlap and fasten said thigh, end cap and patella pieces to said thigh piece.

13. The therapeutic cover apparatus as set forth in claim 11 wherein a plurality of straps containing mating fasteners are displaced along a length of said thigh piece and mount to circumscribe and bind said thigh piece to an amputee's leg.

14. The therapeutic cover apparatus as set forth in claim 11 wherein the plurality of the wings of said thigh piece include a plurality of displaced parallel lines of stitching arranged to segregate each of the plurality of wings into a plurality of tabs and wherein a length of each wing can be tailored without fraying to a circumference of an amputee's limb upon severing one or more tabs from one or more of said plurality of wings at said lines of stitching.

15. The therapeutic cover apparatus as set forth in claim 14 wherein a pair of closely spaced lines of stitching are provided at a distal end of each tab and between which lines of stitching the tab can be severed without fraying.

16. A therapeutic cover apparatus for an amputated leg comprising:

a) a fabric thigh piece having a longitudinal center portion containing a rigid channel member exhibiting a contoured arcuate longitudinal channel space adapted to support an amputee's leg, wherein a plurality of fabric wings having mating fasteners laterally extend from said center portion to wrap about and circumscribe an amputee's leg, overlap and fasten together to encase and secure the thigh piece to an amputee's leg, wherein said plurality of wings include a plurality of displaced parallel lines of stitching arranged to segregate each of the plurality of wings into several tabs such that one or more tabs can be severed between said lines of stitching to tailor a length of each wing to a circumference of an amputee's leg, wherein said thigh piece and plurality of wings are lined with a fleece material, and wherein said channel member is secured in a pocket between an external fabric layer and an internal fleece layer of said center portion;

b) a fleece lined fabric stump contact piece containing a foam pad and adapted to mount to said thigh piece to cushion a stump end of the amputated limb;

c) a fleece lined fabric end cap piece containing a foam pad and adapted to fasten to said thigh piece to cover and cushion a stump end of the amputated limb; and d) a fleece lined fabric patella piece containing a foam cushion and adapted to fasten to said thigh piece to cover and cushion an amputee's patella.

17. The therapeutic cover apparatus as set forth in claim 16 wherein a plurality of straps are mounted to circumscribe an external surface said thigh piece and wherein said straps include mating fasteners.

18. The therapeutic cover apparatus as set forth in claim 16 wherein said thigh, end cap and patella pieces include a plurality of tabs of hook and loop fastener material affixed to surfaces of said fabric and fleece layers to overlap and fasten to said thigh piece.

19. The therapeutic cover apparatus as set forth in claim 16 including a thermal insulation material mounted between selected fabric and fleece layers of said thigh, stump contact, end cap and patella pieces.

* * * * *